United States Patent
Kauphusman et al.

(10) Patent No.: US 7,488,340 B2
(45) Date of Patent: Feb. 10, 2009

(54) VASCULAR ACCESS CLOSURE SYSTEM

(75) Inventors: James V. Kauphusman, Champlin, MN (US); Howard Root, Excelsior, MN (US); Richard Prather, St. Michael, MN (US)

(73) Assignee: Vascular Solutions, Inc., Minneapolis, MN (US)

( * ) Notice: Subject to any disclaimer, the term of this patent is extended or adjusted under 35 U.S.C. 154(b) by 624 days.

(21) Appl. No.: 10/452,826

(22) Filed: Jun. 2, 2003

(65) Prior Publication Data
US 2004/0243052 A1   Dec. 2, 2004

(51) Int. Cl.
*A61B 17/03*   (2006.01)

(52) U.S. Cl. ..................... 606/213
(58) Field of Classification Search ............ 606/213, 606/214, 216, 200, 108, 151, 157, 158; 604/164.04, 604/164.07
See application file for complete search history.

(56) References Cited

U.S. PATENT DOCUMENTS

| | | | |
|---|---|---|---|
| 4,614,945 A | 9/1986 | Brunius et al. | |
| 4,744,364 A | 5/1988 | Kensey | |
| 4,852,568 A | 8/1989 | Kensey | |
| 4,890,612 A * | 1/1990 | Kensey | 606/213 |
| 5,021,059 A | 6/1991 | Kensey et al. | |
| 5,108,421 A | 4/1992 | Fowler | |
| 5,192,301 A * | 3/1993 | Kamiya et al. | 606/213 |
| 5,222,974 A | 6/1993 | Kensey et al. | |
| 5,324,306 A | 6/1994 | Makower et al. | |
| 5,350,399 A | 9/1994 | Erlebacher et al. | |
| 5,372,146 A * | 12/1994 | Branch | 606/232 |
| 5,454,833 A | 10/1995 | Boussignac et al. | |
| 5,507,744 A | 4/1996 | Tay et al. | |
| 5,591,205 A | 1/1997 | Fowler | |
| 5,601,602 A | 2/1997 | Fowler | |
| 5,620,461 A | 4/1997 | Muijs Van de Moer et al. | |
| 5,643,317 A | 7/1997 | Pavcnik et al. | |
| 5,649,959 A | 7/1997 | Hannam et al. | |
| 5,676,689 A | 10/1997 | Kensey et al. | |
| 5,716,375 A | 2/1998 | Fowler | |
| 5,746,755 A | 5/1998 | Wood et al. | |
| 5,782,860 A | 7/1998 | Epstein et al. | |
| 5,810,810 A | 9/1998 | Tay et al. | |
| 5,916,236 A | 6/1999 | Muijs Van de Moer et al. | |
| 5,922,009 A | 7/1999 | Epstein et al. | |
| 5,947,997 A | 9/1999 | Pavcnik et al. | |

(Continued)

*Primary Examiner*—Eduardo C Robert
*Assistant Examiner*—David Comstock
(74) *Attorney, Agent, or Firm*—Patterson, Thuente, Skaar & Christensen, P.A.

(57) ABSTRACT

A sealing device for sealing punctures in blood vessel walls including a flange connected to a flexible stem having an expansion portion in it. The flexible stem is adapted to be accommodated inside a delivery tube. The delivery tube further includes a hand-hold for ease of handling. The sealing device may further include a loader and a cutter. The flange and flexible stem are preferably constructed of a biodegradable material that has a tensile strength, rigidity, memory and other physical qualities similar to medical grade silicone. The resilient transverse expansion portion expands when deployed beyond the delivery tube in the tissue tract to create a frictional interface with the interior surface of the tissue tract to resist displacement of the flexible stem from a desired location in the tissue tract. The flexible stem also includes a flange at the distal end of the flexible stem to seal the puncture when the flexible stem is deployed.

6 Claims, 17 Drawing Sheets

U.S. PATENT DOCUMENTS

| | | |
|---|---|---|
| 5,951,589 A | 9/1999 | Epstein et al. |
| 6,045,569 A | 4/2000 | Kensey et al. |
| 6,063,085 A | 5/2000 | Tay et al. |
| 6,090,130 A | 7/2000 | Nash et al. |
| 6,162,192 A | 12/2000 | Cragg et al. |
| 6,179,863 B1 | 1/2001 | Kensey et al. |
| 6,334,865 B1 | 1/2002 | Redmond et al. |
| 2001/0010005 A1* | 7/2001 | Kammerer et al. .......... 606/213 |

* cited by examiner

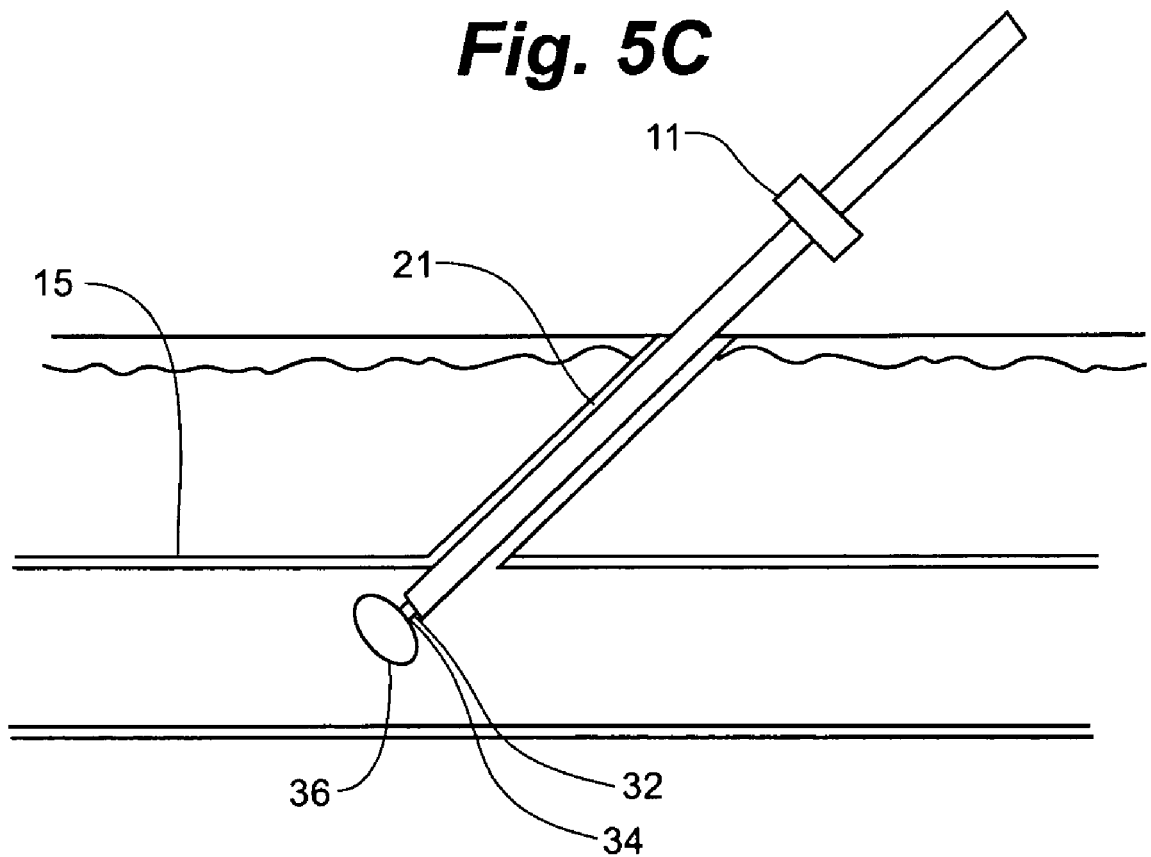

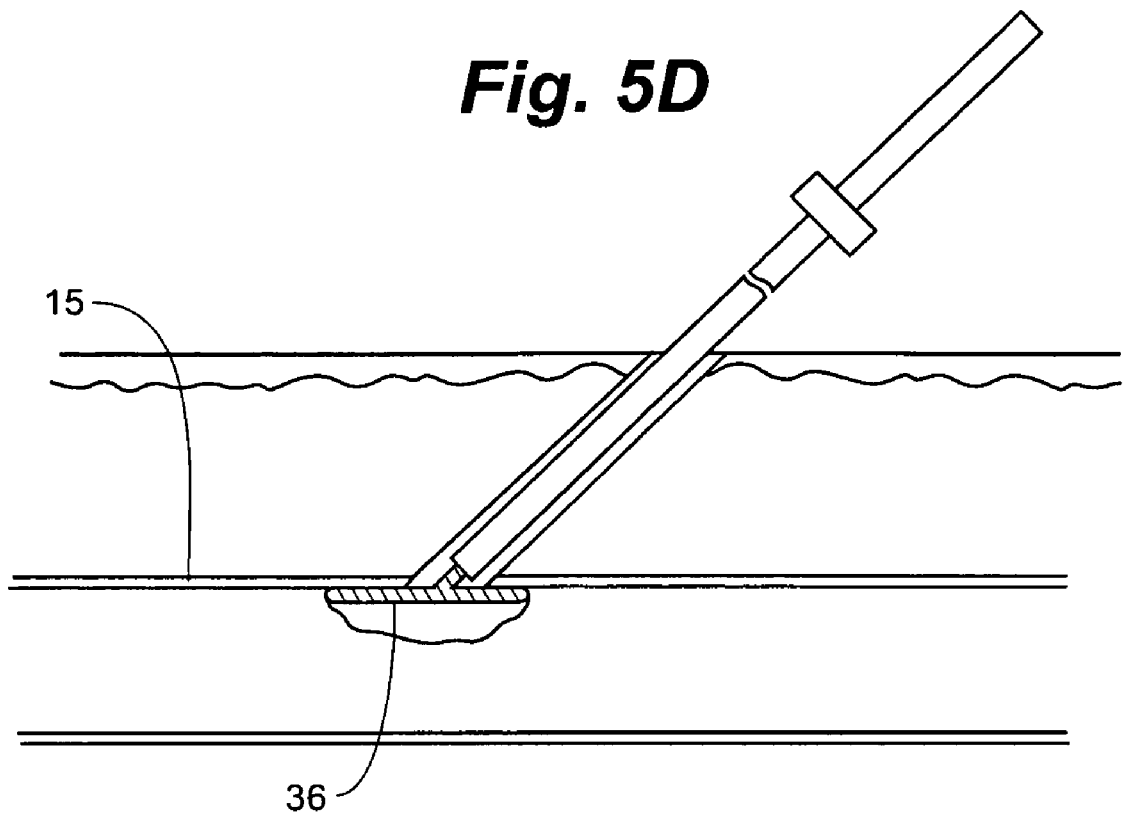

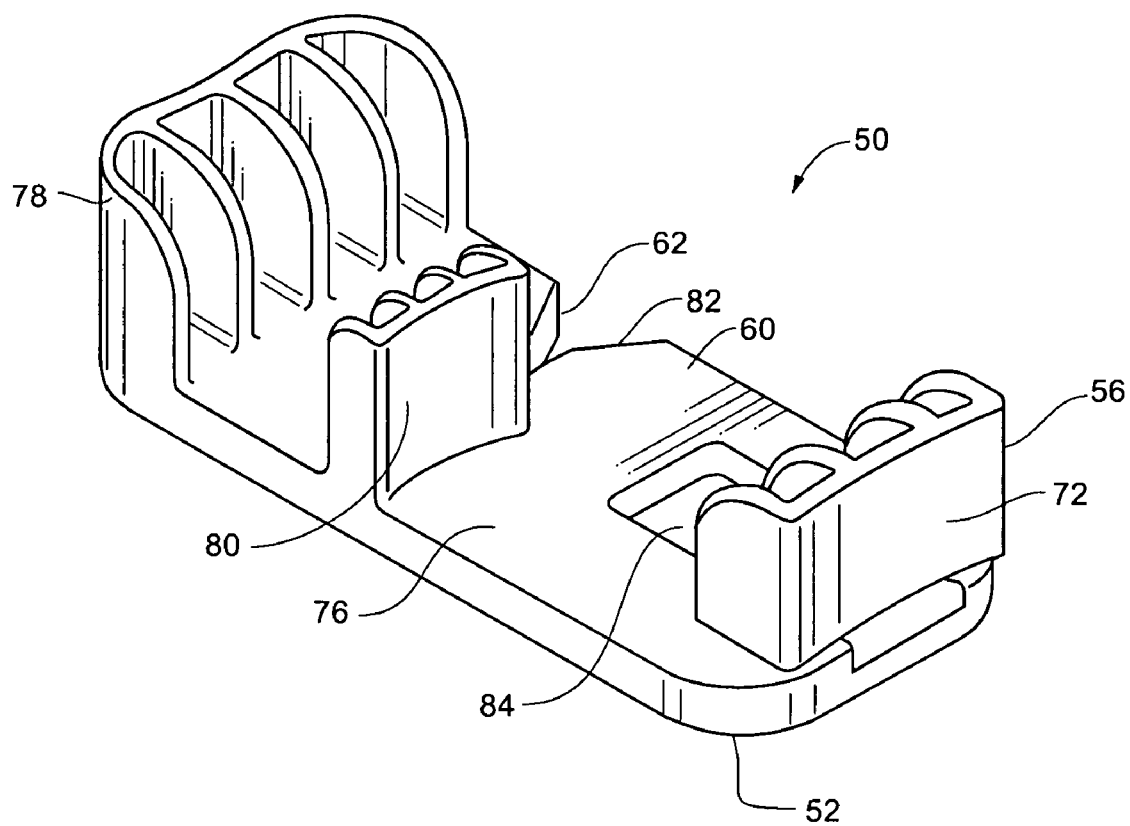

VASCULAR ACCESS CLOSURE SYSTEM

FIELD OF THE INVENTION

The invention generally relates to the field of sealing apertures created by medical procedures that pierce the walls of blood vessels in living tissue.

BACKGROUND OF THE INVENTION

A great many medical procedures in use today involve the insertion of a medical device into a living body in order to pierce a wall of a blood vessel or other similar structure within the body. Examples of such devices include biopsy needles, laparoscopes, trochars, introducers and various other probes that may be inserted into the body. The surgical insertion of such devices creates a wound, which commonly passes through the wall of a blood vessel or other similar tubular structure within the body. When the medical device is withdrawn, an opening is left in the wall of the blood vessel or other tubular structure, which allows for the possibility of the contents of that tubular structure leaking out into the surrounding tissue. In particular, arterial punctures, that is punctures through the wall of an artery, offer the opportunity for significant bleeding because of the relatively high pressure of blood within the artery. Bleeding from a vessel puncture in a substantially sized blood vessel can be severe.

In performing these medical procedures, the medical device pierces the epidermis of the skin and continues to create an incisional tissue tract through tissues intervening between the epidermis and the vessel wall. Finally, the medical device pierces the vessel wall creating a vessel puncture. Typically, a tubular structure holds the tissue tract open to allow for the repeated introduction of instruments into the body during a medical procedure associated with the creation of the vessel puncture. Depending on the context this tubular structure goes by many names, but will be referred to for purposes of this invention as an introducer.

Because vascular access procedures are so common and because the potential complications from failing to effectively seal a vessel puncture can be severe, substantial efforts have been made to resolve the problem of plugging or sealing vessel wall punctures. A variety of different approaches have been used in the art.

One approach is to insert a flat plug on the end of a filament into the blood vessel lumen and to then withdraw the filament in order to pull the plug until it is flush against the interior blood vessel wall. The filament is generally secured to the center of the flat plug. The plug and filament may be made of a biodegradble material that will gradually be absorbed by the surrounding tissue. Once the plug is in place, the filament is tensioned and then secured, typically to the skin on the outside of the body. Examples of this approach include U.S. Pat. Nos. 4,744,364; 4,852,568; 5,021,059; 5,222,974; 5,507,744; 5,643,317; 5,601,602; 5,620,461; 5,676,689; 5,746,755; 5,916,236; 5,947,997 and 6,045,569. Potential problems with this approach are that the point of anchorage may be dislodged or that the filament leading to the outside of the body will provide a continuing path for pathogens creating the possibility of infection. The physician must affirmatively act to fix the device in place. The requirement that the filament be secured to the body exterior adds an additional time-consuming step to the procedure. Tension must be maintained on the filament until it is secured.

Another approach to sealing vessel wall openings is to use cautery via heat radio frequency energy or electrical energy. Examples of this approach include U.S. Pat. Nos. 5,810,810 and 6,063,085. While mostly effective, this approach typically requires more complex and expensive equipment and the success rate is dependent upon the skill of the operator of the equipment.

Several approaches to sealing vessel punctures involve the insertion of material into the tissue tract or vessel. Examples of injecting or inserting a clotting induction agent such as collagen that encourages clotting at the puncture site are shown in U.S. Pat. Nos. 5,591,205; 5,601,602; 6,090,130; 6,162,192; and 6,334,865. Another approach is to place an expanding haemostatic material in the tissue tract outside of the wall of the blood vessel that has been punctured. For example, Gel Foam may be inserted at the location of the juncture of the tissue tract and the vessel wall puncture. Examples in the art taking this approach include U.S. Pat. Nos. 5,108,421; 5,324,306; 5,649,959; and 6,179,863. The challenge with these approaches is preventing the clotting induction agent or expanding hemostatic material from being introduced into the blood vessel itself. The introduction of either agent into the general blood circulation may lead to emboli which will travel with the circulating blood and may lodge in smaller blood vessels leading to interruption of blood flow and ischemia in a remote location. Ischemia can lead to serious consequences.

Yet another approach to closing the vessel puncture is that of inserting a collapsed expansible plug into the blood vessel lumen and then expanding the plug once it is in place. Examples of this approach include U.S. Pat. Nos. 5,350,399; 5,454,833; 5,782,860; 5,922,009 and 5,951,589. These disclosures generally envision an umbrella-like structure that is passed down the tissue tract until it is fully within the vessel lumen. Once within the lumen, the umbrella-like structure is opened and then the portion equivalent to the umbrella handle is withdrawn into the tissue tract in a closed position until the opened canopy structure is snugly against the vessel wall. The entire structure is then secured in place. The umbrella-like structures utilized are rather bulky even in the closed state. This requires that the tissue tract be enlarged beyond what may be necessary for accomplishing the primary medical procedure in order to accommodate the umbrella-like structure. Further, the act of deploying the umbrella-like structure in the vessel lumen may be disadvantageous, particularly as the umbrella-like structure may disrupt the fluid flow within the vessel and thereby encourage thrombus formation.

Lastly, there is an approach to sealing the vessel wall puncture utilizing a small balloon inserted through the tissue tract to block the vessel puncture sited. An example of this approach can be found in U.S. Pat. No. 5,716,375. The balloon is inserted in a deflated state, positioned and then inflated to seal the passage. The challenge with this approach is controlling what happens to the balloon after the puncture is sealed and, like the flat plug embodiments, keeping the balloon secure against the vessel wall while the puncture heals.

The medical arts would benefit from a device that allows for the sealing of blood vessel wall punctures that are created at the termination of a tissue tract that passes through intervening tissues between the vessel wall puncture and a puncture through the skin. It would be preferred if the device was self-securing and small in size so as to be introduced without the need to enlarge the tissue tract beyond the size needed to perform the primary medical procedure.

SUMMARY OF THE INVENTION

The present invention is a sealing device for sealing punctures in vessel walls that has a flange connected to a flexible stem having an expansion portion. The flexible stem and the expansion portion adapted to be accommodated inside a delivery tube. The flange of the present invention is preferably disk shaped and foldable, and may form an integral part of the flexible stem. The flange and stem including the expansion portion are made of a memory material which when distorted tends to return to its pre-distortion shape. When deployed from the delivery tube, the expansion part of the flexible stem resiliently expands and self-anchors in the tissue tract to hold the flange in place against a vessel wall.

In one embodiment, the delivery tube further includes a handhold, and the system is also provided with a funnel/loader and a cutter to facilitate ease of operation. The flange and flexible stem are preferably constructed of a biodegradable material that has a tensile strength, rigidity, memory and other physical qualities similar to medical grade silicone.

Following completion of the primary medical procedure, the primary surgical instrument is removed and the vascular access closure system of the present invention is inserted through the same introducer that was used for the primary medical procedure. The closure system is inserted into the introducer through a loader. The loader is a funnel-like structure which both forms the flange into a folded shape adapted to facilitate placement of the vascular sealing device and protects the flange while the flange is being passed through the introducer. Once the flange has been pushed completely through the introducer and into the blood vessel lumen, it is advanced several millimeters into the blood vessel lumen. This allows the flange to unfold and return to its memory shape. Thereupon, the delivery tube is retracted and the vascular closure device is engaged against the distal end of the introducer. The introducer is retracted until the flange is flattened flush against the interior of the blood vessel wall. Once the flange is flush against the interior blood vessel wall, the introducer is slowly withdrawn from the tissue tract.

As the introducer is withdrawn, the expansion portion of the flexible stem tends to return to its memory shape and expand within the tissue tract. Since the tissue tract limits the expansion of the expansion portion, the expansion portion of the device frictionally grips the interior of the tissue tract securing the flange in place. The expansion portion of the flexible stem may further include friction ridges or barbs on the expansion portion. These friction ridges can serve to provide additional frictional force relative to the interior of the tissue tract.

Once the introducer is completely withdrawn, a cutter may be advanced down the rigid stem or by another route on to the straight portion of the flexible stem whereupon the cutter is used to cut the rigid stem preferably below the skin surface. The remainder of the stem is then withdrawn and the flange and expansion portion are left in place. Because the flexible portion of the device is formed of a biodegradable material, it can remain in place and is degraded by the body and the vessel wall wound and the tissue tract heal.

The expansion portion can take different forms in different embodiments of the invention. For example, the expansion portion may include a series of sigmoid curves, a spiral structure or a multi-winged structure.

BRIEF DESCRIPTION OF THE DRAWINGS

FIG. 5C is a sectional view of the vascular access closure with the flange retracted against the vessel interior wall and with the introducer retracted from the tissue tract;

FIG. 5D is a sectional view of the vascular access closure with the flange retracted against the vessel interior wall;

FIG. 6 is a perspective view of a cutter in accordance with the invention;

DETAILED DESCRIPTION OF THE PREFERRED EMBODIMENTS

Figure 5A:
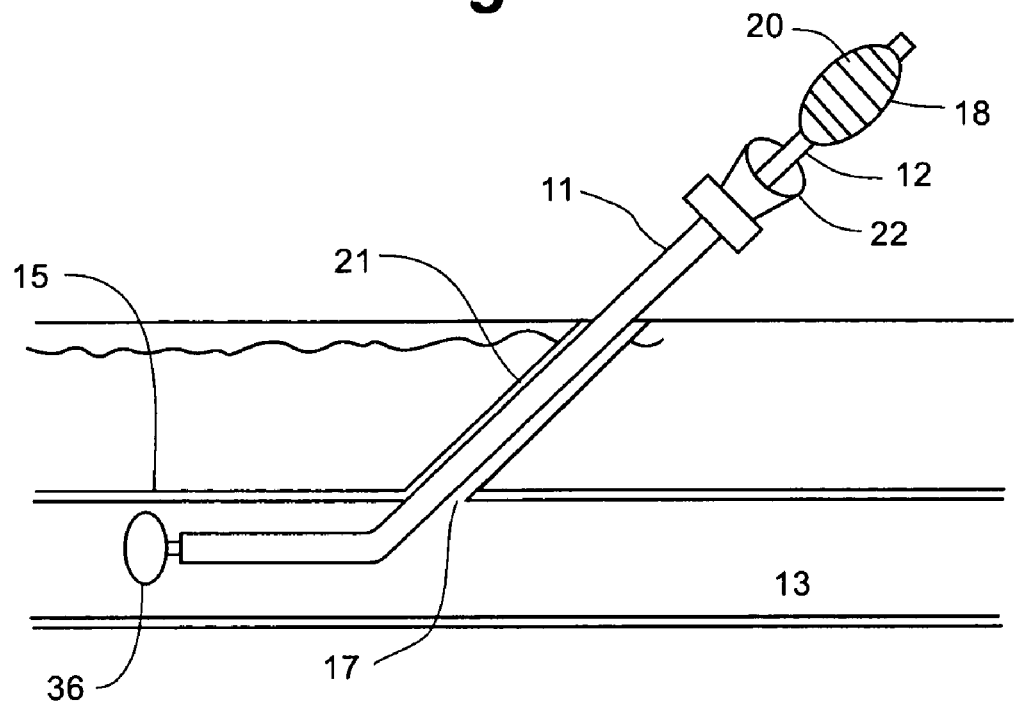
FIG. 5A is a sectional view of the vascular access closure system with the flange inserted into the lumen of a blood vessel prior to retraction.

As shown in FIG. 5A, the vascular access closure system 10 of the present invention is adapted for insertion into a vessel 13, typically via a conventional introducer 11. Vascular access closure system 10 generally includes a delivery tube 12 and a vascular sealing member 14 comprised of a flexible member 32 having a flange 36 that is carried by delivery tube 12. A tissue tract 21 has a distal opening that forms a vessel puncture 17 in a vessel wall 15. The vascular access closure system 10 is utilized to seal the vessel puncture 17 created in the blood vessel wall 15 during various medical procedures, such as the introduction of an introducer 11 into the vessel 13.

Figure 1:
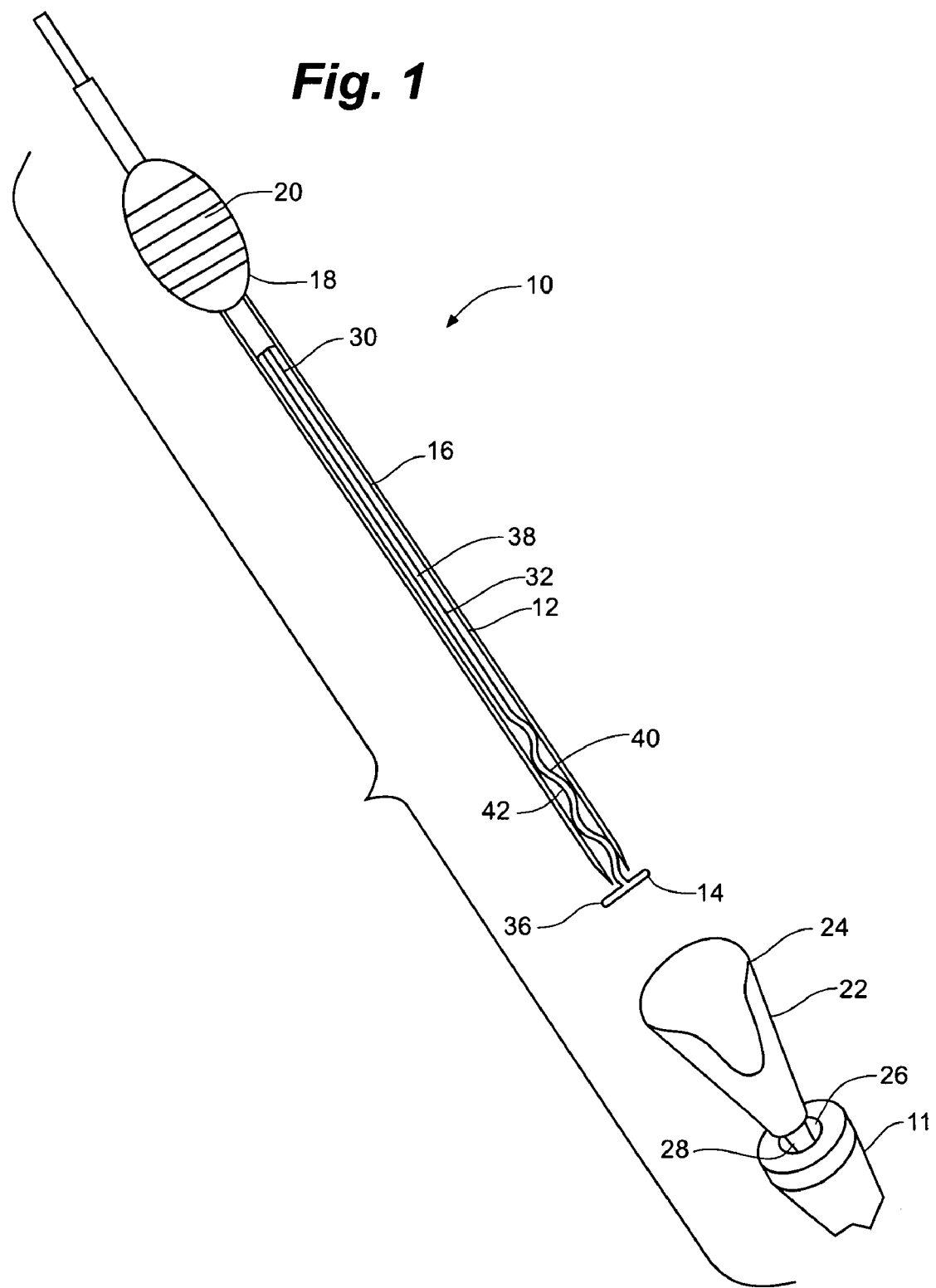
FIG. 1 is a partially cut-away, perspective view of the vascular access closure system in accordance with the invention.
Figure 2:
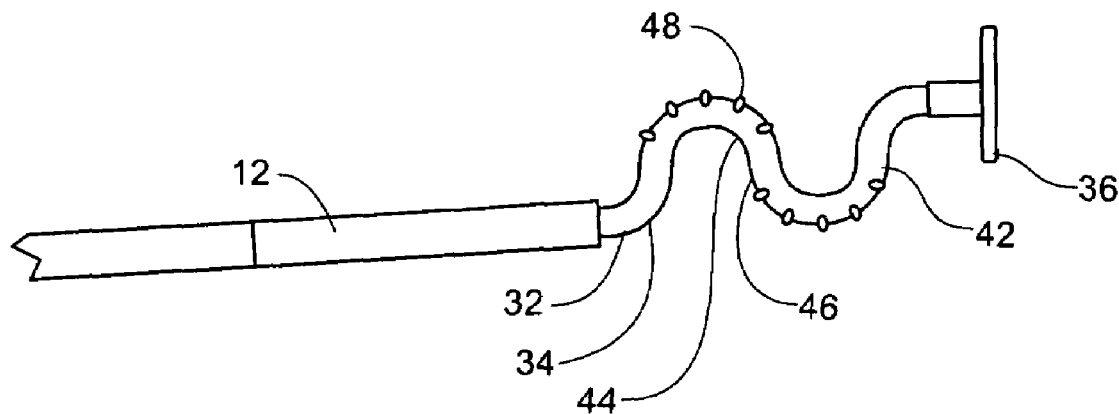
FIG. 2 is a perspective view of the flange and an embodiment of an expansion portion of the flexible stem in an unconstrained state in accordance with the invention.

Referring to FIGS. 1-4, the delivery tube 12 of vascular access closure system 10 preferably is constructed of a semi-rigid material such as a biocompatible polymer. FIG. 1 depicts delivery tube 12 as a straight linear structure, though delivery tube 12 can be made in any curved or other irregular shape as needed to allow desired access to a given vessel location. Delivery tube 12 may have a short tapered section on its distal end. Preferably, the lumen of delivery tube 12 has a circular cross-section, but it will be understood that delivery tube 12 may have one or more lumens in any number of cross-sectional shapes.

Delivery tube 12 generally includes main tube 16 and handhold 18. Main tube 16 is of a length sufficient to reach from the skin surface through introducer 11 and loader 22 down a tissue tract 21 to and beyond the vessel wall 15 that is being accessed into the vessel lumen. Main tube 16 is made of a semirigid material of sufficient rigidity to allow main tube 16 to be guided down a tissue tract 21 independently or through a pre-placed introducer 11. Preferably, a handhold 18 is provided that is appropriately sized and configured to be comfortably held between the thumb and a first or second finger of a physician utilizing the vascular access closure system 10. Handhold 18 is preferably permanently secured to main tube 16, but handhold 18 may also be a removable structure. Handhold 18 may include gripping ridges 20 or a knurled or textured surface in order to facilitate a firm grip for the operator.

In one embodiment, as shown in FIG. 1, vascular access closure system 10 further includes a loader 22 that facilitates loading closure system 10 into a pre-placed introducer 11. Loader 22 generally includes funnel 24 and is adapted to pass through membrane 26. Membrane 26 may be pre-pierced by aperture 28. Loader 22 may define an asymmetric mouth 29 as depicted in FIG. 1. In addition to easing the loading of closure system 10 into the introducer 11, the loader 22 facilitates the asymmetrical folding of flange 36 as the closure system 10 is pushed through the introducer 11. This will be described in more detail below.

Vascular sealing member 14 preferably includes a semirigid stem 30, in addition to the flexible member 32 and the flange 36. Semirigid stem 30 is sized for a snug sliding fit within main tube 16. Semirigid stem 30 may be a tubular structure or a solid structure and is formed from a biocompatible material. Semirigid stem 30 is operably axially coupled with flexible member 32, for example in an abutting end-to-end relation, so as to facilitate deployment of flexible member 32 distally from delivery tube 12.

Flexible member 32 generally includes flexible stem 34 and flange 36. Flexible stem 34 preferably includes a straight portion 38 and a transverse expansion portion 40. Straight portion 38 is of a similar cross-sectional dimension as semirigid stem 30 and is operably axially coupled thereto. Flexible member 32, including flexible stem 34 and flange 36, preferably is made from a biodegradable material which has similar qualities of flexibility and tensile strength as that of medical grade silicone. For example, PHA 3444 (Poly-3-hydroxybutyrate-co-4-hydroxybutyrate) may be utilized Other materials such as polycaprolactone, polydioxinone or any other biodegradable polymer with sufficient tensile strength and flexibility to be used in a suture material application may also be utilized.

For the purposes of the invention as disclosed here, the term biodegradable means that a material is degraded, absorbed or resorbed by the body over a period of time. The term biodegradable as used here includes the terms bioabsorbable and bioresorbable and the meanings of those terms as understood in the art.

Flexible member 32 includes resilient transverse expansion portion 40 proximate a distal end of flexible member 32 that expands in an orientation generally transverse to a longitudinal axis of flexible member 32. When loaded within delivery tube 12, transverse expansion portion 40 is preferably retained in a compressed state and returns to an expanded and relaxed state when deployed distally of delivery tube 12.

Transverse expansion portion 40 may comprise a plurality of sigmoidal curves 42. Each sigmoidal curve 42 includes an inner curvature 44 and an outer curvature 46. Each outer curvature 46 may support friction ridges 48. Friction ridges 48 may include ridges, texturing, indentations or protrusions that increase the frictional quality of outer curvature 46 when it comes into contact with the interior of a tissue tract 21. Preferably, transverse expansion portion 40 includes about one or two s-curves though any number of curves may be utilized.

The diameter of flexible member 32 may range from two French to 20 French. The radius of curvature of outer curvature 46 may vary widely but preferably is from three to five millimeters. Sigmoidal curves 42 may all be positioned in the same plane or may be positioned in various planes. Sigmoidal curves may be symmetric from one curve to the next or may vary in size or radius of curvature.

Figure 14:
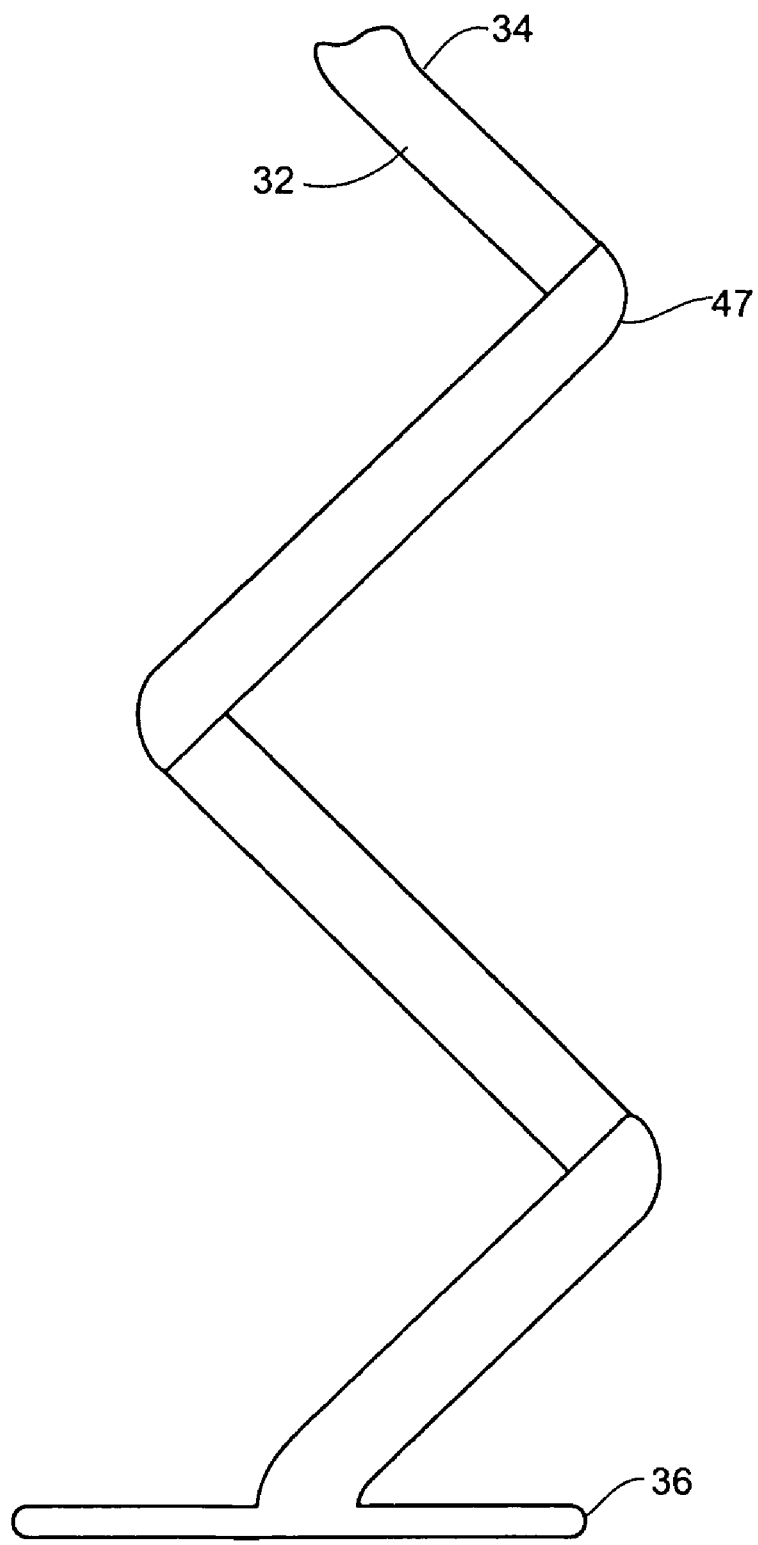
FIG. 14 is a plan view of a second embodiment of the vascular sealing member.

Transverse expansion portion 40 may also take the form of a spiral or helical structure as depicted in FIG. 14. Helix 47 may be cylindrical or conical in form.

Figure 15:
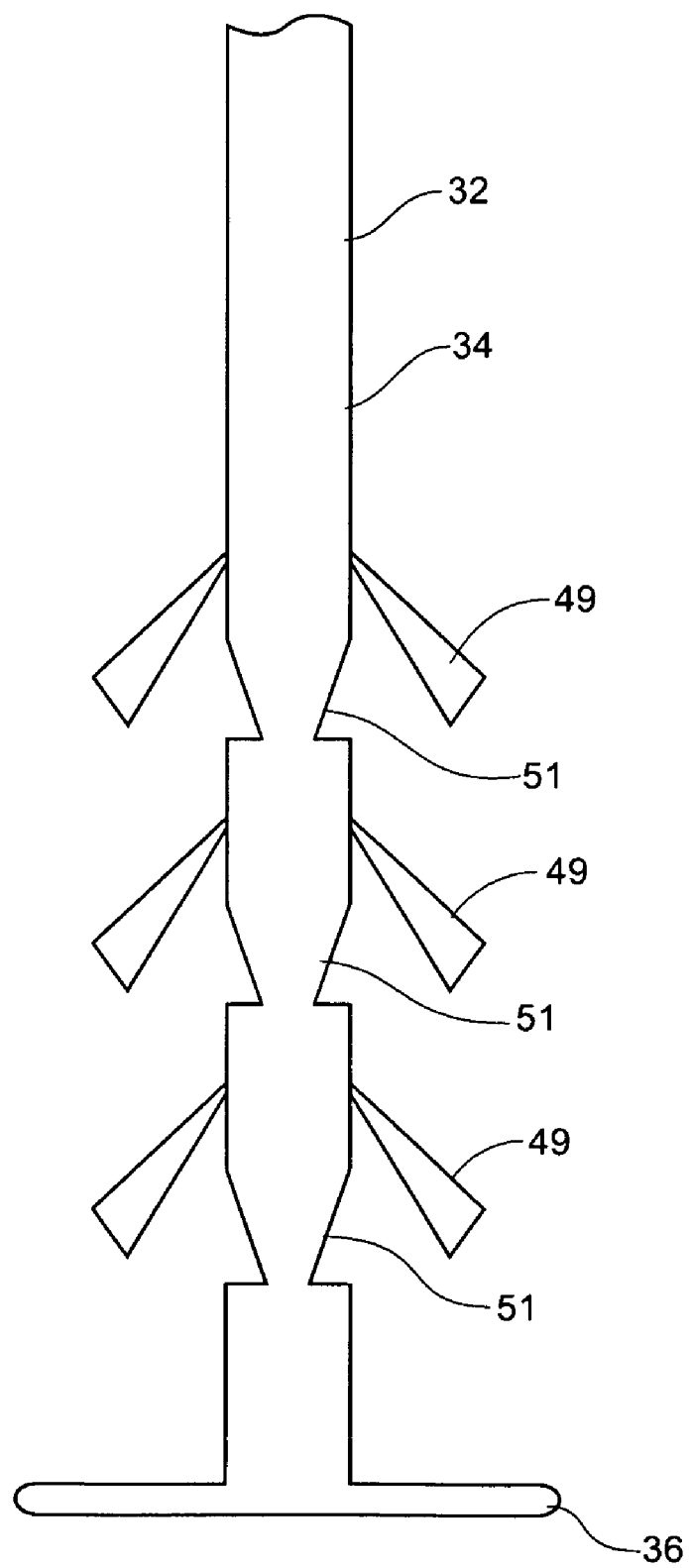
FIG. 15 is a plan view of a third embodiment of the vascular sealing member.

Another option is for expansion portion 40 to take a multi-winged form as depicted in FIG. 15. Multi-winged form includes wings or branches 49 and mating recesses 51. Branches 49 fold or collapse into recesses 51 to allow insertion into delivery tube 12 and resiliently expand to their unfolded shape as depicted in FIG. 15. Branches 49 preferably are shaped to fit into recesses 51 so that when branches are folded expansion portion 40 is generally linear so as to fit smoothly into delivery tube 12.

Branches 49 may be positioned directly opposite one another or may be offset from one another either axially or circumferentially. Branches 49 may also be combined in opposed and offset groups. Branches 49 may also be arranged in a spiral or other three dimensional pattern.

Flange 36 is preferably a flat, thin disk shape operably connected to the distal end of flexible member 32 with flange 36 in a generally planar orientation generally transverse to a longitudinal axis of the flexible member 32. Preferably, flange 36 is formed integrally with flexible stem 34 and is made of the same biodegradable material. Alternatively, flange 36 may be mechanically or adhesively connected to flexible stem 34, or may be fused or welded to flexible stem 34. Preferably, the operable connection of flange 36 to flexible stem 34 is such that the flange 36 may resiliently assume at least two orientations, a sealing orientation that is the relaxed orientation of flange 36 and is generally transverse to the longitudinal axis of flexible member 32 and an asymmetrically folded orientation such as that shown in the cross-section of FIG. 4. Although flange 36 is depicted herein as a circular disk, it may be any shape desired so long as flange 36 has at least one dimension that is greater than a typical width of the vessel puncture 17 such that flange 36 may be positioned to seal substantially all of the vessel puncture 17.

The greatest dimension of the flange 36 may range from two millimeters to fifteen millimeters. Preferably the greatest dimension is about three to seven millimeters. Most desirably, the greatest dimension is about five millimeters. The thickness of the flange preferably is from about 0.1 millimeter to 1.0 millimeters. Preferably, the thickness of flange 36 is about 0.3 millimeters.

In one embodiment, the vascular access closure system 10 further includes a cutter 50. Cutter 50 is adapted to be selectively engaged over semirigid stem 30 and flexible stem 34 in order to sever flexible stem 34, preferably below the skin level but above the level of transverse expansion portion 40. In this embodiment, cutter 50 may be used to compress the skin and the tissue intervening between the skin and the vessel in order to allow the severing of flexible stem 34 below the skin level.

Referring to FIGS. 6, 7, 8 and 9, one embodiment of cutter 50 generally includes base plate 52, blade 54, slider 56, spring 58 and top plate 60. Base plate 52 defines guide notch 62 and blade guide 64. Blade 54 includes cutting edge 66 and engagement aperture 68. Slider 56 includes spring post 70, pusher 72 and blade holder 74. Spring 58 is preferably a compression spring engaged to spring post 70. Spring 58 biases blade 54 away from guide notch 62.

Top plate 60 generally includes body 76, thumb rest 78 and finger rest 80. Top plate 60 also defines guide notch 82 and slider notch 84. Guide notch 82 is similar in shape and dimension to guide notch 62. When the cutter 50 is assembled, guide notch 62 and guide notch 82 align with a space between them to allow the passage of blade 54 between top plate 60 and base plate 52.

Figure 3:
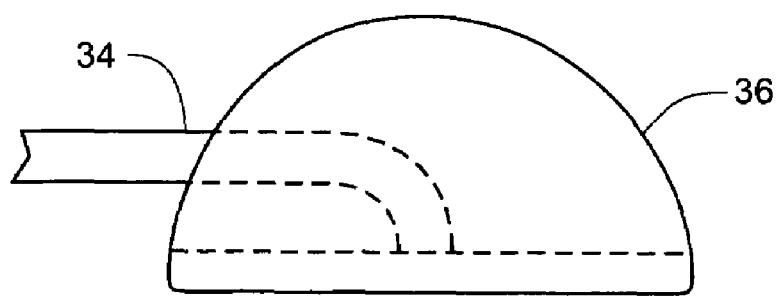
FIG. 3 is a phantom perspective view of the flange in a rolled asymmetrically folded configuration.
Figure 4:
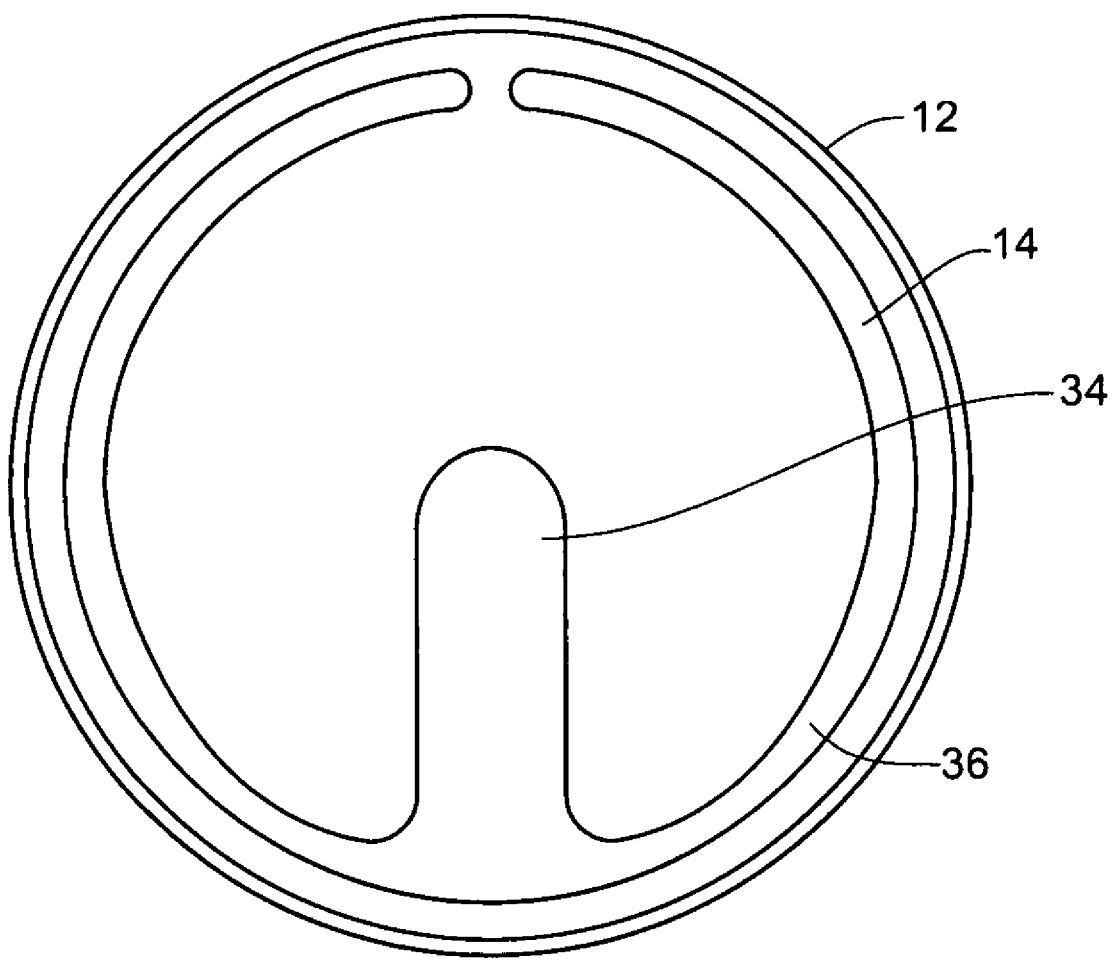
FIG. 4 is an end sectional view of the flange in the rolled asymmetrically folded configuration.

In operation, vascular access closure system 10 is first prepared for use by inserting vascular access closure system 10 into introducer 11. This insertion is facilitated by loader 22. Loader 22 forms flange 36 into an asymmetrically folded configuration as depicted in FIGS. 3 and 4. Loader 22 further protects flange 36 during the loading process. This asymmetrically folded configuration allows flange 36 to pass down a smaller diameter introducer 11 than otherwise might be possible allowing insertion without enlarging the vessel wall puncture. During the process of inserting the vascular access closure system 10 into introducer 11, all parts of the vascular sealing member 14 other than the flange 36 are retracted within delivery tube 12 as depicted in FIG. 1.

The physician then advances the vascular access closure system 10 thru loader 22, down introducer 11 until the flange 36 and delivery tube 12 have advanced through the vessel puncture 17 and into the lumen of the desired vessel 13 as the depicted in FIG. 5A. Preferably, the delivery tube 12 is inserted 3 to 10 millimeters into the vessel lumen distal to the end of introducer 11 to allow flange 36 to resume its undistorted shape and orientation.

Figure 5B:
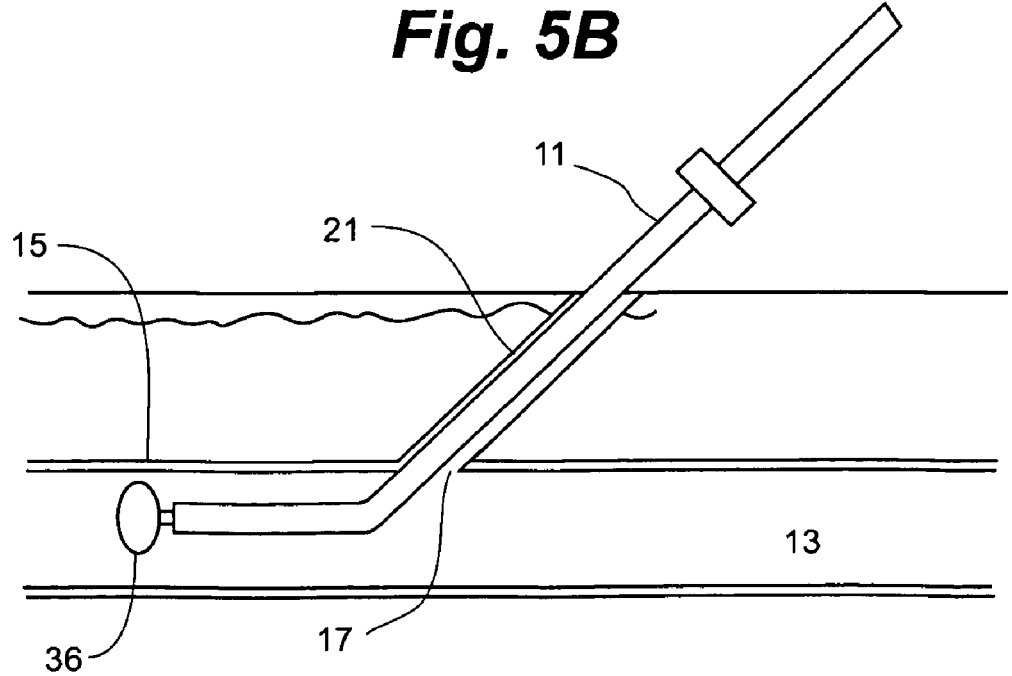
FIG. 5B is a sectional view of the vascular access closure with the flange retracted against the vessel interior wall but with the delivery tube unretracted.

Next, the physician removes the delivery tube 12 flange 36 snugly engaged against the distal opening of introducer 11 as depicted in FIG. 5B. Then, the physician retracts introducer 11 together with delivery tube 12 and continues this operation until flange 36 is snugly engaged against the interior of the vessel wall 15 at the vessel puncture 17. This state is depicted in FIG. 5C.

Once the flange 36 is sealingly engaged with the vessel puncture 17, the physician then withdraws the introducer 11 and retracts the delivery tube 12 so as to expose the transverse expansion portion 40 of flexible member 32 to the inner surface of the tissue tract 21 as depicted in FIG. 5D. These steps may be accomplished simultaneously or in either order such that the end result is the exposure of the transverse expansion portion to the inner surface of the tissue tract 21. The material of the flexible member 32 has a memory that causes it to tend to return to a resiliently expanded state. The transverse expansion portion 40 tends to return to its maximally expanded state thus expanding within the tissue tract 21 and in the preferred embodiment tending toward an undulating configuration that serves to position and secure the flexible member 32 longitudinally within the tissue tract 21.

It should be understood that the sequence of withdrawing the introducer 11, the delivery tube 12 and the flexible stem 34 is not critical to the invention so long as the physician maintains tension on the flexible stem 34 throughout and flange 36 is snugly retracted against vessel wall 15.

In a preferred embodiment, the undulating configuration causes the friction ridges 48 to press against and engage the interior of the tissue tract and to hold the transverse expansion portion 40 in place thus resisting forces that tend to dislodge flange 36 from its desired location flush against the interior of the blood vessel wall 15. Note that friction ridges 48 serve to provide a grip on the interior of the tissue tract 21 in order to maintain flange 36 in snug opposition to the interior of the blood vessel wall 15.

Figure 5E:
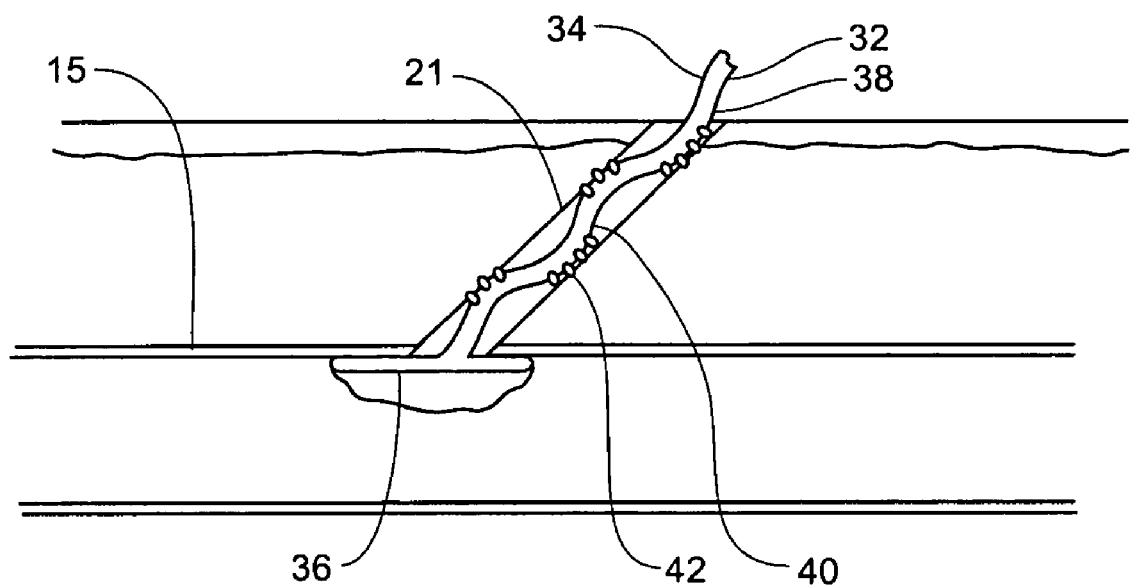
FIG. 5E is a sectional view of the vascular access closure with the flange retracted against the vessel interior wall, the stem severed and in its implanted state.
Figure 7:
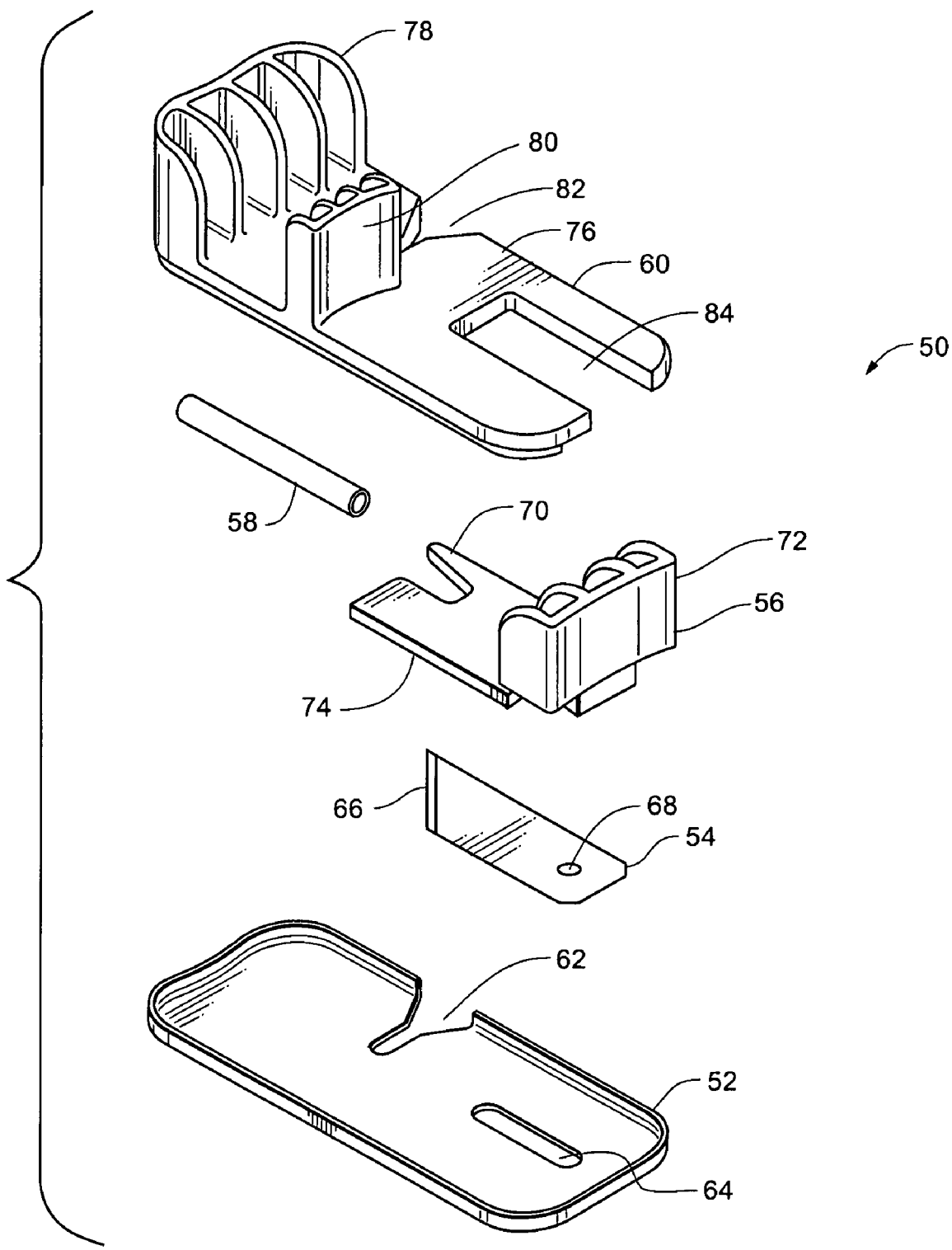
FIG. 7 is an exploded perspective view of the cutter.
Figure 8:
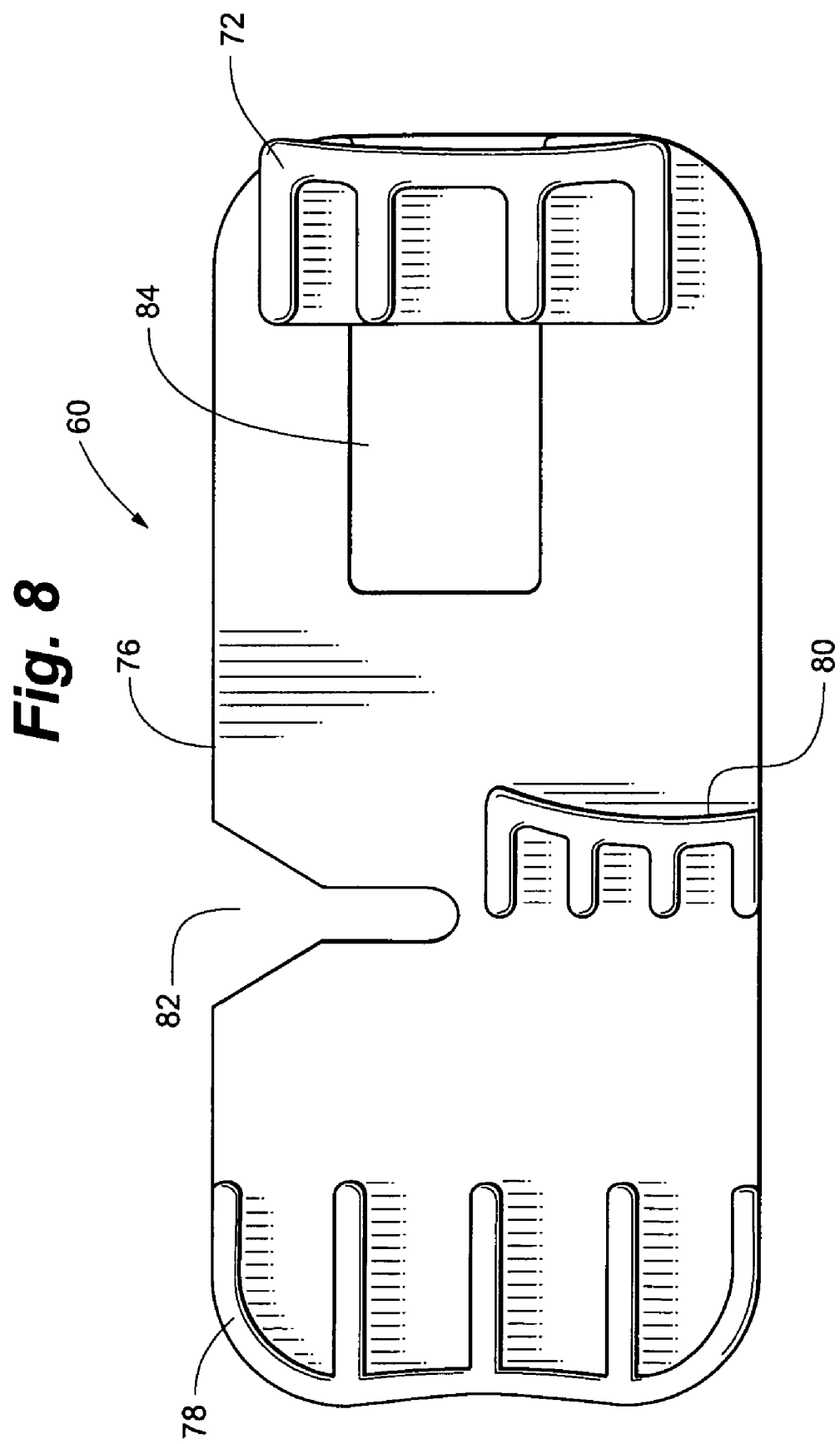
FIG. 8 is a top plan view of the cutter.
Figure 9:
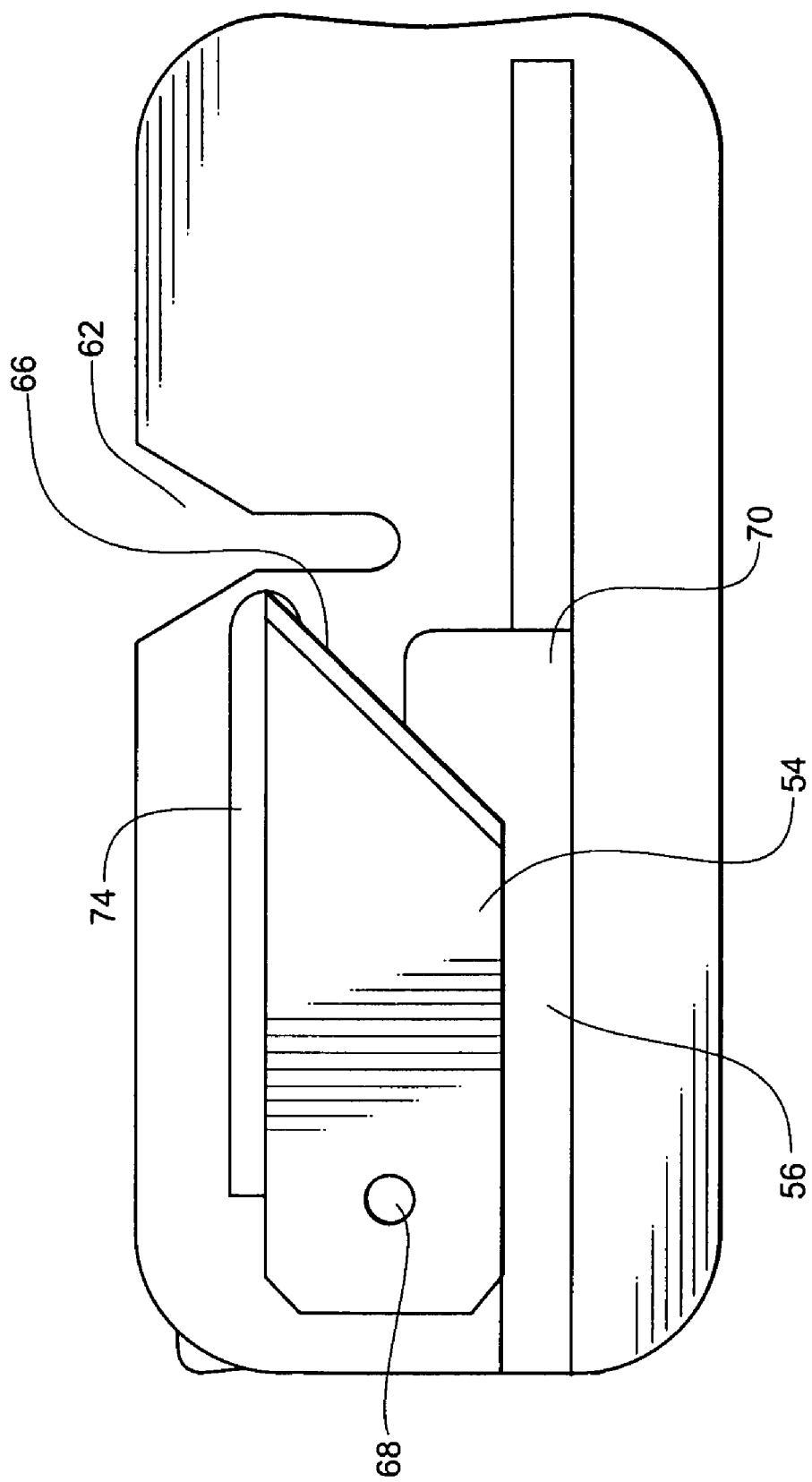
FIG. 9 is a bottom phantom plan view of the cutter
Figure 10:
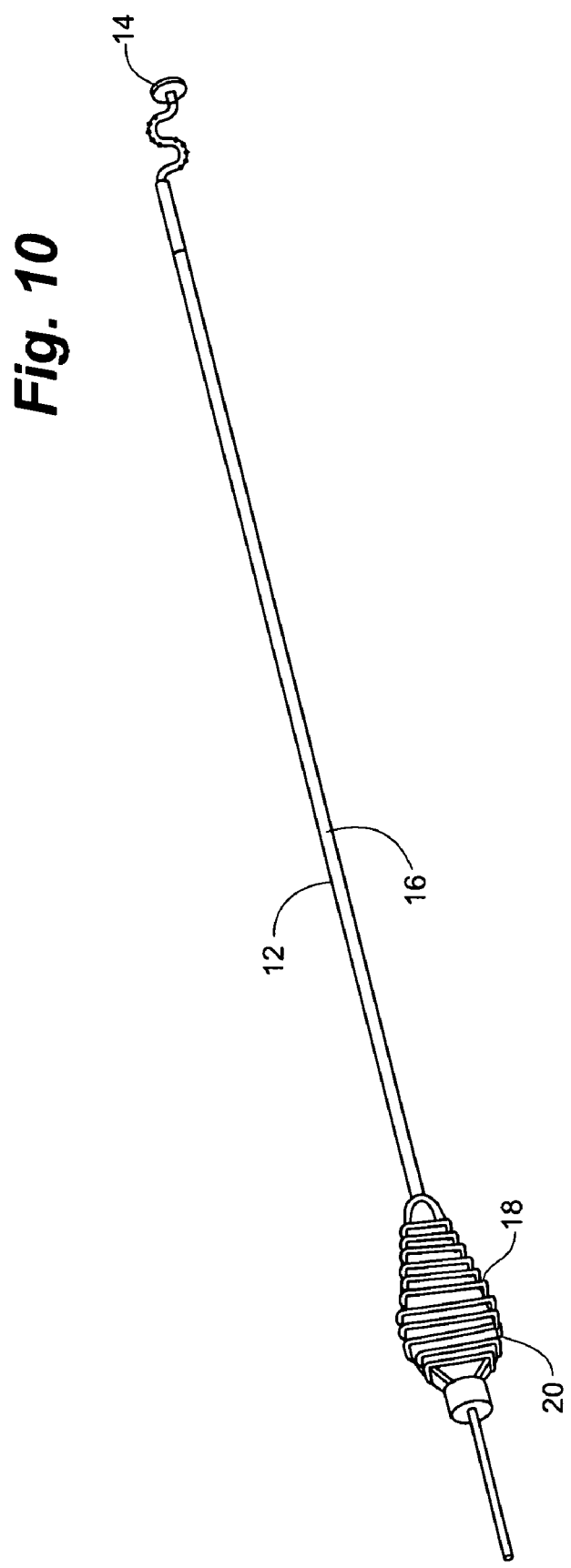
FIG. 10 is a perspective view of the delivery tube and vascular sealing member in accordance with the invention.
Figure 11:
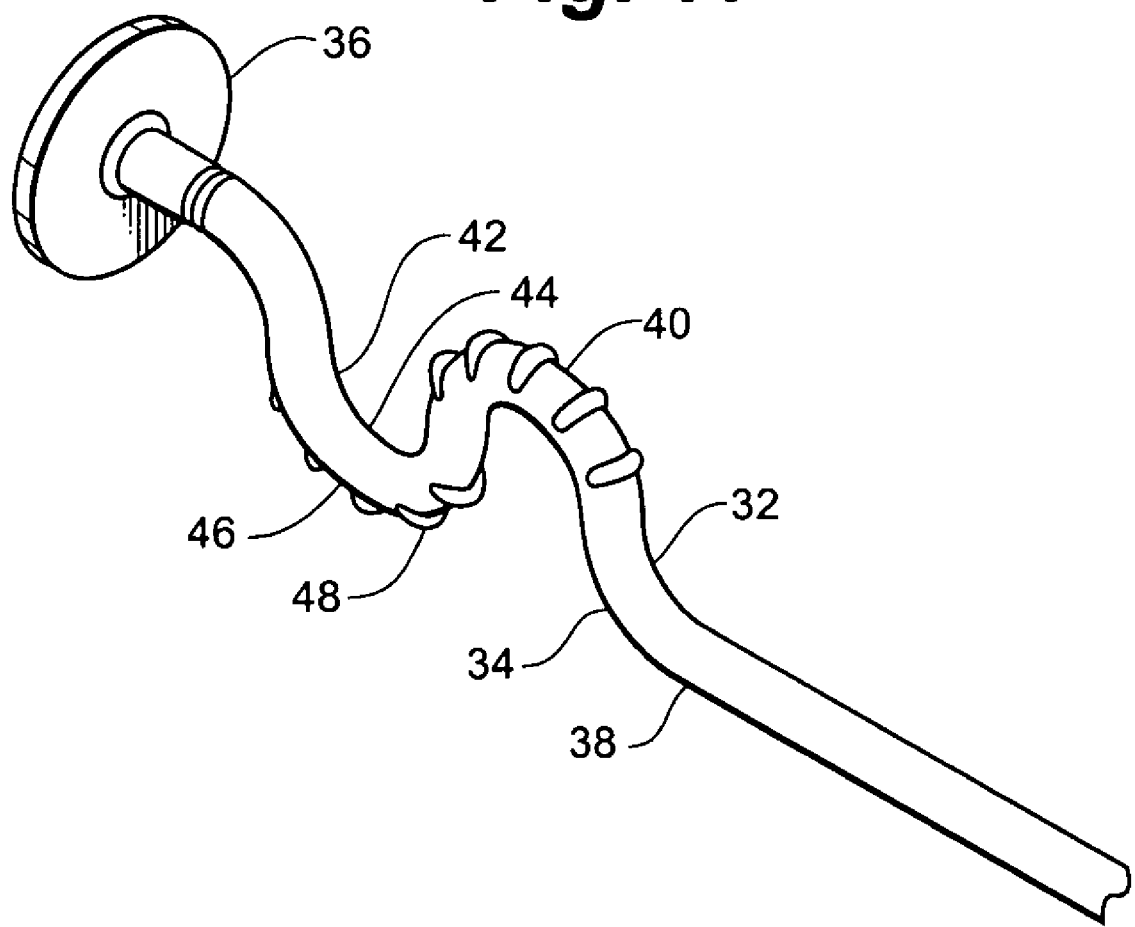
FIG. 11 is a perspective view of the vascular sealing member in accordance with the invention.
Figure 12:
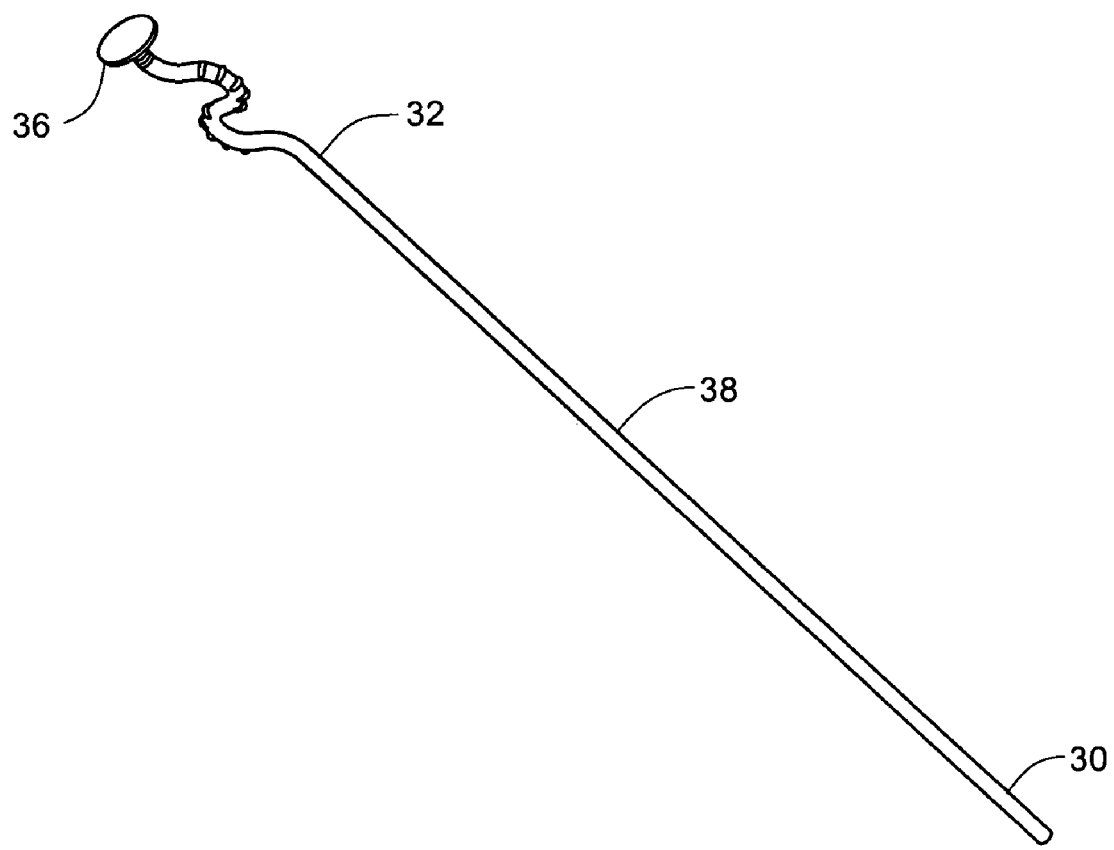
FIG. 12 is another perspective view of the vascular sealing member.
Figure 13:
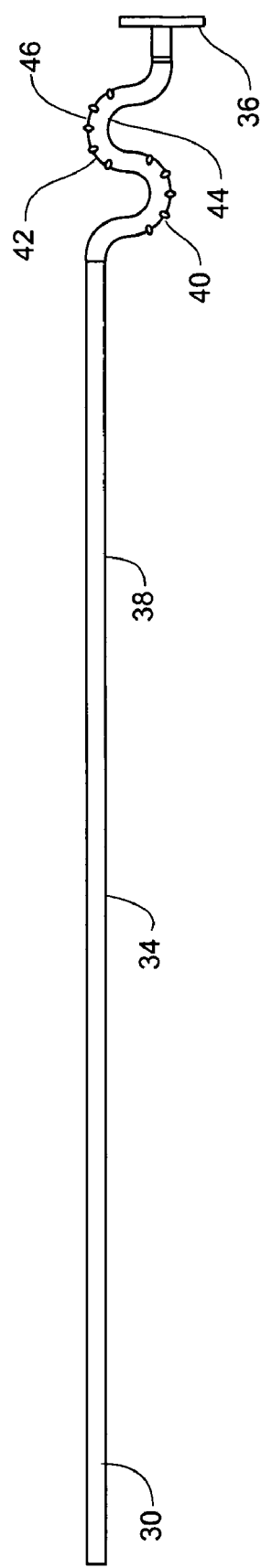
FIG. 13 is a plan view of the vascular sealing member.

In one embodiment, the proximal portion of flexible member 32 may be secured to skin with tape, for example, and the wound be allowed to heal. Preferably, in order to reduce the potential for infection from an exposed portion of the flexible member, the proximal portion of flexible member 32 is cut off. In this embodiment, a cutter 50 is advanced down semirigid stem 30 and onto flexible stem 34. During this process, tension is maintained upon the vascular sealing member 14 and the cutter 50 is pressed firmly against the skin surface compressing the skin and those tissues intervening between the skin and the blood vessel wall 15. Cutter 50 is then activated to sever flexible stem 34 above the level of transverse expansion portion 40. As depicted in FIG. 5E, this leaves the vascular sealing member 14 engaged in place with flange 36 against the blood vessel wall 15 and transverse expansion portion 40 firmly engaged within the tissue tract 21.

When operating the cutter 50, the physician grasps the cutter 50 between the thumb and first finger with the thumb resting on thumb rest 78 and the first finger resting on finger rest 80. The physician then manipulates cutter 50 to insert flexible stem 34 into guide notch 62 and guide notch 82. The physician then presses base plate 52 firmly against the skin to compress the skin and intervening tissues while retaining tension on semirigid stem 30. When cutter 50 is in the desired position, the physician utilizes his second finger to push pusher 72 toward thumb rest 78 to slide blade 54 through guide notch 62 and guide notch 82 to sever flexible stem 34. The surgeon then applies a dressing over the skin puncture and the procedure is complete.

The present invention may be embodied in other specific forms without departing from the central attributes thereof, therefore, the illustrated embodiments should be considered in all respects as illustrative and not restrictive, reference being made to the appended claims rather than the foregoing description to indicate the scope of the invention.

What is claimed is:

1. A method for percutaneously sealing a puncture in a blood vessel wall, the puncture being at the termination of a tissue tract that passes through intervening tissues between the vessel wall puncture and a corresponding puncture through the skin, the method comprising:
   inserting a flexible stem into a delivery tube;
   in the process of inserting the flexible stem into the delivery tube, tensioning the flexible stem so that the flexible stem alters from a transversely expanded state to a generally linear state within the delivery tube;
   inserting the delivery tube including the joined flexible stem into an introducer already placed in the tissue tract, the flexible stem having a flange at a distal end thereof;
   pushing the delivery tube through the introducer until the distal end of the flexible stem is within a lumen of the blood vessel;
   withdrawing the delivery tube from the introducer;
   withdrawing the flexible stem until the flange is flush against the blood vessel wall;
   withdrawing the introducer from the tissue tract; and
   maintaining tension on a portion of the flexible stem by contact between part of the flexible stem and the tissue tract as the flexible stem returns to a transversely expanded state and wherein the flexible stem terminates beneath the skin when the method is completed.

2. The method as claimed in claim 1, further comprising severing the flexible stem at a desired location.

3. The method as claimed in claim 1, further comprising advancing a cutter over the flexible stem to sever the flexible stem.

4. The method as claimed in claim 1, further comprising engaging a loader to the introducer to facilitate the insertion of the delivery tube and the flexible stem into the introducer.

5. The method as claimed in claim 1, further comprising asymmetrically folding the flange while inserting it into the introducer.

6. The method as claimed in claim 1, further comprising utilizing a flexible stem made from a biodegradable material.

* * * * *